(12) United States Patent
Fantucci

(10) Patent No.: US 6,177,571 B1
(45) Date of Patent: Jan. 23, 2001

(54) METHOD FOR REMOVING HEAVY METALS FROM ORGANIC COMPOUNDS

(75) Inventor: Mario Fantucci, Milan (IT)

(73) Assignee: Zambon Group S.p.A., Vicenza (IT)

(*) Notice: Under 35 U.S.C. 154(b), the term of this patent shall be extended for 0 days.

(21) Appl. No.: 09/381,638

(22) PCT Filed: May 4, 1998

(86) PCT No.: PCT/EP98/02629

§ 371 Date: Sep. 27, 1999

§ 102(e) Date: Sep. 27, 1999

(87) PCT Pub. No.: WO98/51647

PCT Pub. Date: Nov. 19, 1998

(30) Foreign Application Priority Data

May 13, 1997 (IT) .............................. MI97A1107

(51) Int. Cl.⁷ .............. C02F 1/52; C07B 63/02; C09B 67/54

(52) U.S. Cl. .................... 548/146; 548/189; 423/22; 423/34; 423/140; 210/665; 210/719; 210/688; 210/705

(58) Field of Search .................... 210/665, 719, 210/688, 705; 423/22, 34, 140; 548/146, 189

(56) References Cited

U.S. PATENT DOCUMENTS

| 4,629,570 | * | 12/1986 | Kennedy, Jr. | ............ 210/666 |
| 4,678,584 | * | 7/1987 | Elfine | ............ 210/719 |
| 4,971,775 | * | 11/1990 | Hoy et al. | ............ 423/140 |

FOREIGN PATENT DOCUMENTS

| 0306436 | 3/1989 | (EP) . |
| 0526997 | 2/1993 | (EP) . |

* cited by examiner

*Primary Examiner*—Richard L. Raymond
*Assistant Examiner*—Pavanaram K. Sripada
(74) *Attorney, Agent, or Firm*—Arent Fox Kintner Plotkin Kahn PLLC

(57) ABSTRACT

A method for removing heavy metals, selected from palladium, tin and nickel, from heavy metal complexes with thiazole compounds in aqueous or alcoholic solution, by precipitation as sulfides, characterised in that such solutions are treated with a water-soluble ammonium, alkaline or alkaline-earth sulfide.

10 Claims, No Drawings

METHOD FOR REMOVING HEAVY METALS FROM ORGANIC COMPOUNDS

This application is a 371 of PCT/EP98/02629 filed May 4, 1998.

The present invention relates to a method for removing heavy metals from organic compounds by precipitation as sulfides and, more particularly, it relates to a method for removing heavy metals from aqueous or hydroalcoholic solutions of organic compounds by precipitation as sulfides.

Heavy metals, such as for example palladium, tin and nickel are extensively used in synthetic industrial processes for preparing various organic compounds useful in many practical fields.

Palladium is the most commonly used heavy metal, especially in coupling reactions.

Because of the high solubility of palladium or other heavy metal complexes, even significant amount of such metals can remain, as hardly removable impurities, within organic compounds.

Therefore, in case that the use of such compounds requires a high degree of purity in terms of heavy metals content, their presence represents a considerable drawback from the industrial point of view.

Such drawback appears to be particularly relevant, for example, in the case of pharmacologically active organic compounds for which it is known that heavy metals content must be particularly low.

For a general reference on methods for detecting heavy metals content in pharmacologically active compounds see, for example, The United States Pharmacopeia, USP 23. NF 18. page 1727 (1995).

In the literature, some processes for removing heavy metals, in particular from industrial waste effluents, are known.

In the U.S. Pat. No. 4,678,584 (Cx/Oxytech. Inc.) a method for removing palladium and other heavy metals from waste water or from other industrial fluids, by precipitation as sulfide, including the use of an alkaline or an alkaline-earth trithiocarbonate as precipitant agent, is described.

Nevertheless the present method appears to be rather tedious as far as the use of the precipitant reagent is concerned, in its turn prepared by reaction of carbon sulfide with a sulfide or an alkaline or alkaline-earth hydroxide.

In our knowledge, methods for removing palladium or other heavy metals from organic compounds involving the use of a sulfide as precipitant agent have not been described in the literature.

Now we have found and it is the object of the present invention a method for removing heavy metals from aqueous or hydroalcoholic solutions of organic compounds, by precipitation as sulfides, characterised in that such solutions are treated with a water-soluble sulfide.

The present method is easily industrially applied and it allows to remove heavy metals efficaciously under particularly smooth reaction conditions.

Such method appears to be widely applicable to a variety of organic substrates and it allows to isolate them with high yield and with a particularly low content of heavy metals, equal to or lower than 10 ppm.

In the present description, if not differently stated, for hydroalcoholic solution we mean an aqueous solution containing $C_1$–$C_4$ lower alcohols, optionally in admixture.

In the hydroalcoholic solution specific alcohols are, for example, methanol, ethanol, isopropanol, n.butanol or mixture thereof.

Preferably, the hydroalcoholic solution comprises methanol, ethanol or their mixture.

The water:alcohol weight ratio in the hydroalcoholic solution is preferably comprised between 1:4 and an upper limit of 100% in water.

The removal of heavy metals, according to the present method, is directly carried out on the aqueous or hydroalcoholic solutions of the organic compounds by their treatment with a soluble sulfide such as, for example, ammonium or an alkaline or alkaline-earth metal sulfide.

Specific usable alkaline or alkaline-earth sulfides are, for example, sodium, lithium, potassium, calcium and magnesium sulfide.

Preferably sodium sulfide is used.

Such compounds are easily disposable and commercially available.

According to the method object of the present invention the selected sulfide is added to the organic compound solution both as solid and, alternatively, as aqueous solution.

Therefore, in that last case, a preformed solution of the selected sulfide will be added to the aqueous or hydroalcoholic solution of the organic compound.

It is evident to the man skilled in the art that the amount of the sulfide to be used depends on the amount of the heavy metal to be removed.

Preferably, the molar ratio sulfide:heavy metal is between 1:1 and 100:1.

From an industrial view-point, amounts of sulfide even greater are similarly effective but useless.

The suspension obtained by addition of the sulfide to the organic compound solution containing the heavy metal, is kept under stirring at the selected temperature and time.

The resultant heavy metal insoluble sulfide is then easily removed from the reaction medium by filtration, according to conventional methods.

The method object of the present invention is widely applicable to different organic compounds soluble in water or in the above hydroalcoliolic solutions.

In view of the foregoing, it is evident to the man skilled in the art that the present method is applicable to the removal of many heavy metals such as, for example, tin, palladium, or other transition metals able to form insoluble sulfides.

More particularly, the current method is applicable to the removal of one or more heavy metals present within organic compounds.

Preferably, the method object of the present invention is used to remove palladium.

For a general reference about the use of palladium in synthetic organic processes see, for example, Jiro Tsuji, Palladium Reagents and Catalysts, John Wiley & Sons (1995).

In particular, palladium is extensively used as catalyst, both in heterogeneous and homogenous catalysis processes.

Catalysts based on palladium in homogenous catalysis processes are, for example, the complexes formed by palladium(0) or palladium(II) in the presence of suitable ligands. in particular triphenylphosphine.

For a general reference about the use of said catalysts see, for example, Chem. Rev. 1995, 95, 2457–2483 and the already mentioned "Palladium Reagents and Catalysts".

The use of such catalysts implies that even relevant quantities of said metal remain in solution, in the reaction medium, as palladium(0) or palladium(II).

Therefore, the isolated reaction products will still contain hardly removable amounts of palladium.

In the International patent application N° 97/07024 entitled "Process for the preparation of heteroaryl-phenylalanines" in the name of the same applicant, a process for the preparation of heteroaryl-phenylalanines of formula

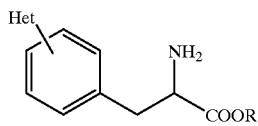

(I)

wherein
R is a hydrogen atom, a $C_1$–$C_4$ linear or branched alkyl group or a benzyl group;
Het is an optionally substituted 5 or 6 member aromatic heterocyclic group with 1 or 2 heteroatoms selected among nitrogen, oxygen and sulfur;
comprising the cross-coupling reaction between a phenylalanine derivative and a heteroaryl-zinc halide, in the presence of a palladium(0) based catalyst, is described.

The resultant compounds of formula I can be used as intermediates for the synthesis of pharmacologically active derivatives.

Therefore, in a preferred embodiment, the method object of the present invention is used for removing palladium from the aqueous or hydroalcoholic solutions of heteroaryl-phenylalanines of formula I, optionally as acid addition salts, described in the above-mentioned International patent application.

In a preferred embodiment of the process object of the present invention, a suitable amount of the selected sulfide in aqueous solution is added to an appropriate amount of an aqueous or hydroalcoholic solution of the organic compound, for example a compound prepared according to a palladium catalysed cross-coupling process.

The resultant suspension is kept under vigorous stirring at room temperature for the selected time.

Subsequently, the formed palladium sulfide is removed by filtration through a celite pad.

By working according to standard isolation techniques, for example by extraction in the presence of an organic solvent, separation of the phases and removal of the organic phase solvent, the desired compound is obtained with high yield and with a palladium content equal to or lower than 10 ppm.

The so treated organic compounds can for example be used directly as such, or as synthetic intermediates, for the preparation of pharmacologically active derivatives.

The method object of the present invention is easily industrially practicable and allows to remove palladium and other heavy metals from organic compounds in aqueous or hydroalcoholic solutions efficaciously, by employing commonly used and easily disposable precipitant reagents, as the above cited sulfides.

Besides, such a method is carried out under smooth reaction conditions and can be widely applied to a variety of organic substrates.

With the aim to illustrate the present invention the following examples are now given.

EXAMPLE 1

Removal of palladium from 4-(2-thiazolyl)-L-phenylalanine methyl ester dihydrochloride in the presence of sodium sulfide nonahydrate Sodium sulfide nonahydrate (15 g. 0.06 moles) and charcoal (35 g) were added to a solution of 4-(2-thiazolyl)-L-phenylalanine methyl ester dihydrochloride (821 g 2.14 moles) in water (1.6 l), prepared as described in the International patent application N° 97/07024 in the name of the same applicant, kept under nitrogen at room temperature.

The suspension was kept under stirring at a temperature of 20–25° C. for 30 minutes and, subsequently, after addition of celite (20 g) and filtration, the residue was washed with water (2×0.1 l).

Toluene (1.3 l) and a 28% ammonium hydroxide aqueous solution (0.45 l) were added to the resultant yellow-orange aqueous solution up to pH 8. keeping the temperature at 20–25° C.

The mixture was kept under stirring for 30 minutes at room temperature and the phases were separated.

The separated organic phase was evaporated under reduced pressure at 60° C. giving 4-(2-thiazolyl)-L-phenylalanine methyl ester (0.52 g: HPLC titre 94.2%) as solid product with a palladium content lower than 10 ppm.

EXAMPLE 2

Removal of palladium from 4-(2-thiazolyl)-L-phenylalanine methyl ester dihydrochloride in the presence of sodium sulfide nonahydrate and ammonium hydroxide Sodium sulfide nonahydrate (2.76 g; 0.0115 moles) and after 5 minutes, a 30% ammonium hydroxide solution (0.0256 l), up to pH 3–3.5 were added to a solution of 4-(2-thiazolyl)-L-phenylalanine methyl ester dihydrochloride (128.5 g: 0.38 moles) in water (0.257 l). prepared as described in example 1 and containing 2700 ppm of palladium.

After 5 minutes under stirring, decolorizing charcoal (6 g) was added and after further 15 minutes the suspension was filtered through a celite pad, washing the residue with water (3×0.02 l).

The filtrate, kept under stirring at room temperature. was alkalinised up to pH 8 by adding potassium hydrogencarbonate (42.2 g) and afterwards extracted with methytene chloride (200 ml).

The organic phase was dried on sodium sulfate and evaporated to dryness furnishing 4-(2-thiazolyl)-L-phenylalanine methyl ester (100 g), as oily residue with a palladium content lower than 10 ppm.

EXAMPLE 3

Removal of palladium and tin from 4-(2-thiazolyl)-L-phenylalanine methyl ester dihydrochloride in the presence of an aqueous solution of sodium sulfide A solution of sodium sulfide nonahydrate (50 g; 0.21 moles) in water (0.25 l) was added to a solution of 4-(2-thiazolyl)-L-phenylalanine methyl ester dihydrochloride (278 g; 0.83 moles) in water (2 l), prepared starting from tin-derivatives in the presence of a palladium(0) based catalyst, as described in the International patent WO 97/24342 in the name of the same applicant, and containing 690 ppm of tin and 250 ppm of palladium.

After 1 hour under stirring at room temperature, the resultant suspension was filtered on a celite pad, washing the residue with water (3×0.1 l).

The filtrate, kept under stirring at room temperature, was alkalinised up to pH 8 by adding potassium hydrogencarbonate (200 g) and afterwards extracted with methylene chloride (1 l and 0.5 l).

Decolorizing earth (50 g) was then added to the combined organic phases, washed with water (0.15 l) and dried on sodium sulfate.

The mixture was filtered under vacuum and the residue was washed with methylene chloride (3×0.2 l).

The resultant solution was evaporated to dryness giving 4-(2-diazolyl)-L-phenylalanine methyl ester (183 g), as oily residue with a palladium and tin content lower than 10 ppm.

What is claimed is:

1. A method for removing heavy metals, selected from palladium, tin and nickel, from heavy metal complexes with thiazole compounds in aqueous or alcoholic solution, by precipitation as sulfides, characterised in that such solutions are treated with a water-soluble ammonium, alkaline or alkaline-earth sulfide.

2. A method according to claim 1 for removing palladium.

3. A method according to claim 1 wherein the alcoholic solution is an aqueous solution containing $C_1$–$C_4$ lower alcohols, optionally in admixture.

4. A method according to claim 3 wherein the lower alcohols are selected between methanol and ethanol.

5. A method according to claim 1 wherein the water:alcohol weight ratio in the alcoholic solution is comprised between 1:4 and an upper limit of 100% in water.

6. A method according to claim 1 wherein the sulfide is sodium sulfide.

7. A method according to claim 1 wherein the aqueous or alcoholic solutions are treated with the water-soluble sulfide in aqueous solution.

8. A method according to claim 1 wherein the molar ratio of sulfide; heavy metal is between 1:1 and 100:1.

9. A method for removing palladium from thiazolyl-phenylalanin of formula

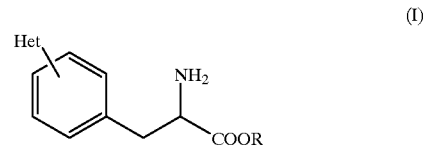

(I)

wherein

R is a hydrogen atom, a $C_1$–$C_4$ linear or branched alkyl group or a benzyl group;

Het is an optionally substituted thiazolyl;

in aqueous or alcoholic solution, by precipitation as sulfide, characterised in that such solutions are treated with a water-soluble ammonium, alkaline or alkaline-earth sulfide.

10. A method according to claim 1, wherein the sulfide is selected from the group consisting of sodium sulfide, lithium sulfide, potassium sulfide, calcium sulfide, and magnesium sulfide.

* * * * *